United States Patent [19]

Fuss et al.

[11] Patent Number: 4,727,142
[45] Date of Patent: Feb. 23, 1988

[54] PROCESS FOR THE PREPARATION OF IMIDATES

[75] Inventors: Andreas Fuss, Karlstein; Günter Siegemund, Hofheim am Taunus, both of Fed. Rep. of Germany

[73] Assignee: Hoechst Aktiengesellschaft, Frankfurt am Main, Fed. Rep. of Germany

[21] Appl. No.: 853,635

[22] Filed: Apr. 18, 1986

[30] Foreign Application Priority Data

Apr. 22, 1985 [DE] Fed. Rep. of Germany ....... 3514450

[51] Int. Cl.$^4$ ............... C07C 119/18; C07C 119/20; C07D 401/00; C07D 409/00
[52] U.S. Cl. ........................... 544/216; 558/1; 558/2; 558/4; 558/5; 558/6; 558/8; 546/272; 546/281; 546/283; 546/284; 546/291; 546/331; 546/334; 546/261; 548/178; 548/561; 548/565; 548/566; 549/451; 549/75; 544/336; 544/335; 544/224
[58] Field of Search ............ 558/1, 2, 4, 5, 6, 8; 546/261, 272, 281, 283, 284, 291, 331, 334; 548/178, 561, 565, 566; 549/451, 75; 544/216, 336, 335, 224

[56] References Cited

U.S. PATENT DOCUMENTS

| | | | |
|---|---|---|---|
| 2,091,257 | 8/1937 | Eckelmann et al. | 558/1 |
| 2,686,802 | 8/1954 | Slack et al. | 558/1 |
| 2,953,563 | 9/1960 | Schaefer et al. | 558/6 |
| 3,492,375 | 1/1970 | Gruber et al. | 558/1 |

FOREIGN PATENT DOCUMENTS

| | | | |
|---|---|---|---|
| 2147794 | 9/1971 | Fed. Rep. of Germany | 546/192 |
| 3334207A1 | 9/1983 | Fed. Rep. of Germany | 558/8 |

OTHER PUBLICATIONS

Neilson, Douglas G., "The Chemistry of Amidines and Imidates", John Wiley & Sons, (1975), pp. 385–394.
Houben-Weyl, "Methoden der Organischen Chemie", Band VIII, pp. 697–701.

Primary Examiner—Alan L. Rotman
Assistant Examiner—Robert C. Whittenbaugh
Attorney, Agent, or Firm—Curtis, Morris & Safford

[57] ABSTRACT

The invention relates to a process for the preparation of compounds of the formula I and salts or acid addition compounds thereof

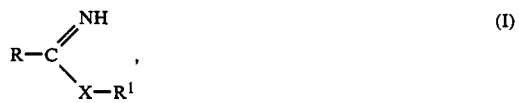

in which
R denotes hydrogen, (halogenated) alkyl with the exception of CF$_3$, a (substituted) aromatic radical, (substituted) heteroaryl, (substituted) phenoxy, (substituted) phenylthio, (substituted) phenylamino, halogen, hydroxyl, alkoxy, mercapto, (halogenated) cycloalkyl, alkylmercapto, amino, monoalkylamino or dialkylamino,
R$^1$ denotes (substituted alkyl, (substituted) phenyl or naphthyl, alkenyl, alkinyl, cycloalkyl, (substituted) benzyl or heteroaryl, and X denotes oxygen or sulfur, which comprises reacting a nitrile of the formula II with a compound of the formula III

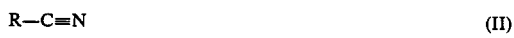

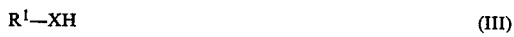

in the presence of anhydrous hydrofluoric acid, a perfluoroalkanecarboxylic acid, a perfluoralkanesulfonic acid or a perfluorinated ion exchanger containing sulfonic acids, and converting the resulting salts of the formula I, if appropriate by the addition of bases, into the free imidates of the formula I and, if approximate, converting the latter subsequently into further salts or acid addition compounds. The invention also relates to the new compounds of the formula I in which R$^1$ denotes a (substituted) phenyl radical and R and X have the meanings mentioned. The compounds of the formula I are valuable intermediate products in the preparation of plant protection agents and pharmaceuticals.

13 Claims, No Drawings

PROCESS FOR THE PREPARATION OF IMIDATES

The invention relates to a new process for the preparation of imidates.

The preparation of imidates from nitriles and alcohols under the conditions of the Pinner reaction is known. Only hydrogen chloride, hydrogen bromide, hydrogen iodide or sulfuric acid are used as reactants in this reaction. Owing to the sensitivity to heat of the imidate salts initially formed, the reaction temperature is limited to low reaction temperatures (0° to 5° C.) (see, for example, D. G. Nelson in S. Patai, The Chemistry of Amidines and Imidates, John Wiley & Sons, 1975, page 385). As a result of the low reaction temperatures, long reaction times must be accepted.

Furthermore, ortho-substituted benzonitriles, such as, for example, o-tolunitrile, 2-chlorobenzonitrile, 2-fluorobenzonitrile or 2,6-difluorobenzonitrile (cf. H. Henecka and P. Kurtz in Houben-Weyl-Müller, Methoden der Organischen Chemie, ("Methods of Organic Chemistry"), Thieme Verlag, Stuttgart, volume 8, 1952, page 697) cannot be employed or result in unsatisfactory yields in this Pinner reaction. In addition, only an incomplete reaction or no reaction at all is also observed in the case of sterically hindered nitriles or nitriles containing electron-attracting substituents, such as trichloroacetonitrile. Difficulties also arise when tertiary alcohols are used as reactants.

A new process for the preparation of imidates has now been found, which has a wider applicability and has technical advantages in use.

The invention relates, therefore, to a process for the preparation of compounds of the formula I and salts thereof or acid addition compounds

in which

R denotes hydrogen, $(C_1-C_{20})$-alkyl, halogenated $(C_1-C_{20})$-alkyl with the exception of $CF_3$, naphthyl, anthracenyl or phenyl or phenyl, anthracenyl or naphthyl, all three of which are monosubstituted or polysubstituted by halogen, hydroxyl, $(C_1-C_6)$-alkyl, $(C_1-C_6)$-alkylmercapto, $(C_1-C_6)$-alkoxy, $(C_1-C_6)$-alkylsulfonyl, $(C_1-C_6)$-alkylsulfinyl or $(C_1-C_6)$-alkylsulfonyloxy, it being possible for the abovementioned alkyl-containing radicals to be halogenated, halogen, nitro, $(C_1-C_6$-alkoxy)-carbonyl, cyano, phenyl, phenylthio or phenoxy, it being possible for these three radicals to be substituted in turn by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or halogen; heteroaryl which can be substituted by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or haloge; phenoxy, phenylthio or phenylamino, it being possible for these three radicals to be substituted by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or halogen; or $(C_3-C_7)$-cycloalkyl which can be halogenated, halogen, hydroxyl, $(C_1-C_{10})$-alkoxy, mercapto, $(C_1-C_{10})$-alkylmercapto, amino, mono-$(C_1-C_{10}$-alkyl)-amino or di-$(C_1-C_{10}$-alkyl)-amino, $R^1$ denotes $(C_1-C_{12})$-alkyl which can be monosubstituted or polysubstituted by halogen, nitro, $(C_1-C_4)$-alkoxy or carboxyl, phenyl or naphthyl both of which can be monosubstituted or polysubstituted by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or halogen; $(C_3-C_6)$-alkenyl, $(C_3-C_6)$-alkinyl, $(C_5-C_6)$-cycloalkyl or benzyl which can be substituted in the phenyl ring by $(C_1-C_6)$-alkyl, $(C_1-C_6)$-halogenoalkyl, $(C_1-C_6)$-alkoxy $(C_1-C_6)$-halogenalkoxy, phenyl, heteroaryl or halogen; or heteroaryl which can be substituted by $(C_1-C_6)$-alkyl, $(C_1-C_6)$-halogenoalkyl, $(C_1-C_6)$-alkoxy, $(C_1-C_6)$-halogenoalkoxy or halogen, and X denotes oxygen or sulfur, which comprises reacting a nitrile of the formula II with a compound of the formula III

in the presence of anhydrous hydrofluoric acid, a perfluoroalkanecarboxylic acid, a perfluoroalkanesulfonic acid or a perfluorinated ion exchanger containing sulfonic acids, and converting the resulting salts of formula I, if appropriate with the addition of bases, into the free imidates of formula I and, if appropriate, subsequently converting the latter into further salts or acid addition compounds.

Suitable salts of the formula I are salts with inorganic acids, such as HCl, HBr, HI, sulfuric acid, phosphoric acid or organic carboxylic acids, such as the perfluoroalkanecarboxylic acids mentioned above, perfluoroalkanesulfonic acids, tetrafluoroboric acid, hexafluorophosphoric acid, picric acid and $(C_1-C_6)$-alkanesulfonic acids;

acid addition compounds are obtained, in particular, by means of hydrofluoric acid, several molecules of HF adding onto the compound of the formula I. The preparation of the salts from the imidates of the formula I is effected by customary methods with which those skilled in the art are familiar.

Amongst the acids used in the reaction of the compounds of the formula II with the compounds of the formula III, use is made, in particular, of hydrofluoric acid and trifluoromethanesulfonic acid and particularly preferentially hydrofluoric acid. The hydrofluoric acid used must be substantially anhydrous. Its water content must not be higher than 1% by weight. The commercial product ®Nafion (made by DuPont, Wilmington) can be employed in the process according to the invention as a perfluorinated ion exchanger containing sulfonic acids.

Suitable heteroaryl radicals for R in formula I are, in principle, heteroaryl radicals which are stable to acids, such as, for example, optionally substituted imidazolyl, pyrazolyl, triazolyl, thiazolyl, oxazolyl, pyridyl, dioxotetrahydropyridyl, triazinyl, pyrimidinyl, pyrazinyl, pyridazinyl, quinolinyl, benzthiazolyl(oxy), quinoxalinyl(oxy), thienyl, furanyl, pyrrolyl and pyrrolidinyl. Halogen radicals are to be understood, in particular, as fluorine or chlorine radicals.

It is preferable to prepare, by the process according to the invention, compounds of the formula I in which R denotes $(C_1-C_{20})$-alkyl, phenyl which can be substituted by $(C_1-C_6)$-alkyl, $(C_1-C_6)$-halogenoalkyl, halogen or hydroxyl, $(C_3-C_7)$-cycloalkyl which can be halogenated or pyridyl, pyrrolyl, furyl, thienyl or dioxotetrahydropyridyl, it being possible for these heterocyclic radicals to be substituted by $(C_1-C_4)$-alkyl, $(C_1-C_6)$-halogenoalkyl, $(C_1-C_6)$-alkoxy, $(C_1-C_6)$-halogenoalkoxy or halogen, $R^1$ denotes $(C_1-C_{12})$-alkyl which can be monosubstituted or polysubstituted by halogen and/or monosubstituted by nitro or carboxyl, phenyl which can be substituted by $(C_1-C_6)$-alkyl, $(C_1-C_6)$-halogenoalkyl, $(C_1-C_6)$-alkoxy, $(C_1C_6)$-halogenoalkoxy or halogen, $(C_5-C_6)$-cycloalkyl, naphthyl or $(C_3-C_6)$-alkenyl or pyridyl or benzthiazolyl both of which can be substituted by $(C_1-C_6)$-alkyl or halogen, and X denotes O or S.

The process according to the invention can be carried out within a wide range of temperature from $-20°$ to $+200°$ C., preferably from 50° to $+150°$ C. The reaction can be carried out under normal pressure or in an autoclave under pressures of 0 to 100 bar.

It is preferable to add a Lewis acid in the reaction between the compounds of the formula II and III. The following are examples of suitable Lewis acids: antimony pentachloride, antimony trifluoride, phosphorus pentachloride, phosphorus trichloride, titanium tetrachloride, iron (III) chloride, aluminum trichloride, zinc dichloride, boron trifluoride, boron trichloride, tin (IV) chloride or copper (I) chloride. The proportion of catalyst, relative to 1 mole of nitrile of the formula II employed, can vary within the range between 0.001 and 1.0 mole.

Instead of the abovementioned Lewis acid catalysts, it is also possible to use an aromatic compound substituted by trichloromethyl, such as benzotrichloride; this is used in a ratio of 0.01 to 1.0 mole per mole of nitrile of the formula II. It is also possible to add, as a catalyst, a mineral acid, such as HCl, HBr or HI, in amounts of 0.01 to 1.0 mole per mole of nitrile.

A solvent is not absolutely necessary for the process according to the invention. In principle, however, it is possible to use inert solvents, such as ethers, halogenated hydrocarbons, aromatic compounds, sulfoxides or sulfones or excess acid.

The reactions are carried out in a simple manner by initially taking the compounds of the formulae II and III, if appropriate together with the catalyst and/or the solvent, under an inert gas atmosphere in a steel or nickel autoclave or in a kettle made of a suitable material, and pumping in the acid. The solvent and the acid are removed by distillation after the reaction. The recovered acid or solvent can be employed again in the reaction.

The imidates of the formula I can be isolated in the form of their salts with the acids used in the reaction or can be obtained as the free base by means of an aqueous base, such as, for example, potassium carbonate or potassium hydroxide. The imidates of the formula I can be purified by distillation. However, it is advantageous to precipitate them in ether in the form of hydrochlorides by means of hydrogen chloride or in the form of tetrafluoroborates by means of $HBF_4$.

Surprisingly, the process according to the invention also takes place in a high yield when using nitriles which only result in unsatisfactory reactions in the process of the state of the art. In addition, it is possible to increase the space-time yield in the process according to the invention greatly. The process is, therefore, also suitable for the preparation of imidates on an industrial scale.

The imidates of the formula I or salts thereof prepared by the process according to the invention are suitable for use as precursors in the synthesis of plant protection agents (see German Offenlegungsschrift No. 3,334,207) or drugs (see German Offenlegungsschrift No.2,147,794).

Some of the imidates prepared by the process of the application are new. These are the compounds of the formula I in which $R^1$ denotes a phenyl radical or, as indicated above, a substituted phenyl radical, and R and X have the meanings mentioned above. These new compounds of the formula I are also an embodiment of the present invention.

The invention is illustrated by means of the examples below.

EXAMPLE 1

1.39 g (10 mmol) of 2,6-difluorobenzonitrile were dissolved at 0° C. in 2 ml of anhydrous hydrofluoric acid in a 10 ml stainless steel autoclave, and 0.92 g (20 mmol) of ethanol was added. The mixture was stirred at 100° C. for 17 hours and allowed to cool, and the volatile constituents were removed by evaporation at 50°–60° C. The residue was dissolved in 20 ml of $H_2O$ and 100 ml of ether, and the aqueous phase was neutralized to phenolphthalein with 40% strength aqueous KOH.

The aqueous phase was extracted with 25 ml of ether, and the combined organic phases were dried over sodium sulfate. The product was then precipitated as the hydrochloride by passing in dry hydrogen chloride gas. 1.22 g (55%) of 0-ethyl 2,6-difluorophenylimidate hydrochloride were obtained as a colorless, crystalline solid, melting point 126°–129° C.

EXAMPLE 2

1.03 g (10 mmol) of benzonitrile, 2 ml of anhydrous hydrofluoric acid and 691 mg (15 mmol) of ethanol were stirred at 100° C. in a stainless steel autoclave for 17 hours as described under Example 1. The contents of the autoclave were cooled and poured onto 25 g of ice and the residual product was rinsed from the autoclave with $H_2O$ and ether. The aqueous phase was neutralized with aqueous potassium carbonate, and the product was extracted with ether.

After the organic phases had been dried over sodium sulfate and the volatile constituents had been removed by evaporation on a rotary evaporator, the product 0-ethyl phenylimidate remained as a colorless oil.

EXAMPLES 3–8

General Instructions (a) mol of 2-chlorobenzonitrile and (b) mol of catalyst were dissolved in 2 ml of HF in a 10 ml stainless steel autoclave, and (c) mol of ethanol were added. The reaction time and temperature and the molar amounts can be seen in Table 1 below. Working up was carried out as described under Example 1. 0-ethyl 2-chlorophenylimidate hydrochloride, melting point 105°–106° C. (decomposition) was obtained as the product in each case.

TABLE 1

| Example | a | b/catalyst | c | Time [hrs.] | Temperature [°C.] | Yield [g] |
|---|---|---|---|---|---|---|
| 3 | $10^{-2}$ | — | $1 \times 10^{-2}$ | 17 | 110 | 1.02 |
| 4 | $10^{-2}$ | — | $1 \times 10^{-2}$ | 1 | 110 | 0.22 |

TABLE 1-continued

| Example | a | b/catalyst | c | Time [hrs.] | Temperature [°C.] | Yield [g] |
|---|---|---|---|---|---|---|
| 5 | $10^{-2}$ | $10^{-3}$/SbCl$_5$ | $1.1 \times 10^{-2}$ | 17 | 70 | 1.43 |
| 6 | $10^{-2}$ | — | $1 \times 10^{-2}$ | 5 | 140 | 1.25 |
| 7 | $10^{-2}$ | $10^{-3}$/TiCl$_4$ | $2 \times 10^{-2}$ | 17 | 70 | 1.50 |
| 8 | $10^{-2}$ | $10^{-3}$/PCl$_5$ | $2 \times 10^{-2}$ | 17 | 70 | 1.63 |

EXAMPLES 9–17

General Instructions (a) mol of the compound of the formula II together with (b) mol of the compound of the formula III and (c) mol of phosphorus pentachloride were stirred in 2 ml of HF in a 10 ml stainless steel autoclave at 70° C. for 17 hours as described in Table 2 below. Working up was carried out as described under Example 1.

The compounds of Examples 18–46 can also be prepared analogously.

TABLE 2

| Example | Compound II | a | Compound III | b | c | Yield [g] | Melting point °C. |
|---|---|---|---|---|---|---|---|
| 9 | 2-methylbenzonitrile (CN, CH$_3$) | $10^{-2}$ | EtOH | $2 \times 10^{-2}$ | $10^{-3}$ | 0.85 | 104–106 (decomp.) |
| 10 | 2-(trifluoromethyl)benzonitrile (CN, CF$_3$) | $10^{-2}$ | EtOH | $2 \times 10^{-2}$ | $10^{-3}$ | 0.47 | 103–105 (decomp.) |
| 11 | 2-hydroxybenzonitrile (CN, OH) | $10^{-2}$ | EtOH | $2 \times 10^{-2}$ | $10^{-3}$ | 1.50 | 137 (decomp.) |
| 12 | t-Bu—CN | $10^{-2}$ | EtOH | $2 \times 10^{-2}$ | $10^{-3}$ | 0.71 | 133–135 (decomp.) |
| 13 | 2,6-difluorobenzonitrile (F, CN, F) | $10^{-2}$ | C$_6$H$_5$OH | $2 \times 10^{-2}$ | $10^{-3}$ | 0.64 | 106–108 (decomp.) |
| 14 | 2,6-difluorobenzonitrile (F, CN, F) | $10^{-2}$ | C$_6$H$_5$SH | $2 \times 10^{-2}$ | $10^{-3}$ | 0.40 | 220–232 |
| 15[1] | 2,6-difluorobenzonitrile (F, CN, F) | $10^{-2}$ | EtSH | $2 \times 10^{-2}$ | $10^{-3}$ | 1.13 | 254–261 |
| 16 | 2,4-dichlorobenzonitrile (CN, Cl, Cl) | $10^{-2}$ | EtOH | $2 \times 10^{-2}$ | $10^{-3}$ | 0.78 | 186–188 |
| 17 | pyridine-2-carbonitrile (N, CN) | $10^{-2}$ | EtOH | $2 \times 10^{-2}$ | $10^{-3}$ | 1.16 | 145–147 |
| 18 | C$_3$H$_7$—CN | | EtOH | | | | |
| 19 | CH$_2$=CH—CN | | EtOH | | | | |

TABLE 2-continued
| Example | Compound II | a | Compound III | b | Yield c | [g] | Melting point °C. |
|---|---|---|---|---|---|---|---|
| 20 | 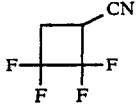 | | EtOH | | | | |
| 21 | $C_{16}H_{33}-CN$ | | EtOH | | | | |
| 22 | $C_6F_5-CN$ | | EtOH | | | | |
| 23 | 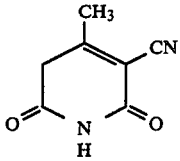 | | EtOH | | | | |
| 24 | HCN | | EtOH | | | | |
| 25 | 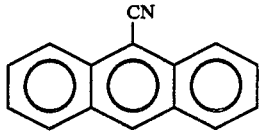 | | EtOH | | | | |
| 26 | 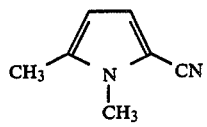 | | EtOH | | | | |
| 27 | 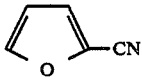 | | EtOH | | | | |
| 28 | 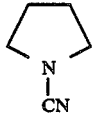 | | EtOH | | | | |
| 29 | 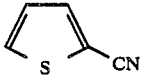 | | EtOH | | | | |
| 30 | 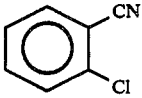 | | $CH_2=CH-CH_2OH$ | | | | |
| 31 | 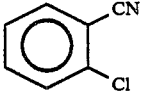 | | $C_{11}H_{23}OH$ | | | | |
| 32 | 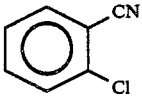 | | 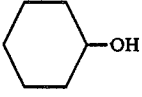 | | | | |
| 33 | 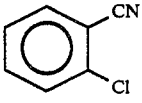 | | $CF_3CH_2OH$ | | | | |

TABLE 2-continued

| Example | Compound II | a | Compound III | b | Yield c | [g] | Melting point °C. |
|---|---|---|---|---|---|---|---|
| 34 | 2-chloro-benzonitrile | | (CF₃)₂CH—OH | | | | |
| 35 | 2-chloro-benzonitrile | | C₈F₁₇CH₂CH₂CH | | | | |
| 36 | 2-chloro-benzonitrile | | O₂N—CH₂CH₂OH | | | | |
| 37 | 2-chloro-benzonitrile | | Cl₃CCH₂OH | | | | |
| 38 | 2-chloro-benzonitrile | | CH₃O—CH₂CH₂OH | | | | |
| 39 | 2-chloro-benzonitrile | | HO₂C—CH₂OH | | | | |
| 40 | 2-chloro-benzonitrile | | 3-hydroxypyridine | | | | |
| 41 | 2-chloro-benzonitrile | | 2-naphthol | | | | |
| 42 | 2-chloro-benzonitrile | | C₆F₅—OH | | | | |
| 43 | 2-chloro-benzonitrile | | CH₂=CH—CH₂—SH | | | | |
| 44 | 2-chloro-benzonitrile | | HO₂C—CH₂SH | | | | |
| 45 | 2-chloro-benzonitrile | | 2-mercaptobenzothiazole | | | | |

TABLE 2-continued

| Example | Compound II | a | Compound III | b | Yield c | [g] | Melting point °C. |
|---|---|---|---|---|---|---|---|
| 46 | 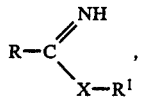 | | <br> | | | | |

[1]Precipitated as the tetrafluoroborate.

We claim:

1. A process for the preparation of compounds of the formula I and salts or acid addition compounds thereof $$R-C\begin{matrix}NH\\ \diagdown\\ X-R^1\end{matrix} \quad (I)$$

in which

R denotes hydrogen, $(C_1-C_{20})$-alkyl, halogenated $(C_1-C_{20})$-alkyl with the exception of $CF_3$, naphthyl, anthracenyl or phenyl or phenyl, anthracenyl or naphthyl, all three of which are monosubstituted or polysubstituted by halogen, hydroxyl, $(C_1-C_6)$-alkyl, $(C_1-C_6)$-alkylmercapto, $(C_1-C_6)$-alkoxy, $(C_1-C_6)$-alkylsulfonyl, $(C_1-C_6)$-alkylsulfinyl or $(C_1-C_6)$-alkylsulfonyloxy, it being possible for the above-mentioned alkyl-containing radicals to be halogenated, halogen, nitro, $(C_1-C_6$-alkoxy)-carbonyl, cyano, phenyl, phenylthio or phenoxy, it being possible for these three radicals to be substituted in turn by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or halogen; heteroaryl which can be substituted by $(C_1-C_6)$-alkyl, $(C_1-C_6)$-halogenoalkyl, $(C_1-C_6)$-alkoxy, $(C_1-C_6)$-halgenoalkoxy, phenyl, heteroaryl or halogen; phenoxy, phenylthio or phenylamino, it being possible for these three radicals to be substituted by $(C_1-C_6)$-alkyl, $(C_1-C_6)$-halogenoalkyl, $(C_1-C_6)$-alkoxy, $(C_1-C_6)$-halogenoalkoxy, phenyl, hereroaryl or halogen; or $(C_3-C_7)$-cycloalkyl which can be halogenated; halogen, hydroxyl, $(C_1-C_{10})$-alkoxy, mercapto, $(C_1-C_{10})$-alkylmercapto, amino, mono-$(C_1-C_{10}$-alkyl)-amino and di-$(C_1-C_{10}$-alkyl)-amino, $R^1$ denotes $(C_1-C_{12})$-alkyl which can be monosubstituted or polysubstituted by halogen, nitro, $(C_1-C_4)$-alkoxy or carboxyl, phenyl or naphthyl both of which can be monosubstituted or polysubstituted by $(C_1-C_6)$-alkyl, $(C_1-C_6)$-halogenoalkyl, $(C_1-C_6)$-alkoxy, $(C_1-C_6)$-halogenoalkoxy, phenyl, heteroaryl or halogen, $(C_3-C_6)$-alkenyl, $(C_3-C_6)$-alkinyl, $(C_5-C_6)$-cycloalkyl or benzyl which can be substituted in the phenyl ring by $(C_1-C_6)$-alkyl, $(C_1-C_6)$-halogenoalkyl, $(C_1-C_6)$-alkoxy, $(C_1C_6)$-halogenoalkoxy, phenyl, heteroaryl or halogen, or heteroaryl which can be substituted by $(C_1-C_6)$-alkyl, $(C_1-C_6)$-halogenoalkyl, $(C_1-C_6)$-alkoxy, $(C_1-C_6)$-halogenoalkoxy or halogen, and X denotes oxygen or sulfur, which comprises reacting a nitrile of the formula II with a compound of the formula III $$R-C\equiv N \quad (II)$$

$$R^1-XH \quad (III)$$

in the presence of anhydrous hydrofluoric acid, a perfluoroalkanecarboxylic acid, a perfluoroalkanesulfonic acid or a perfluorinated ion exchanger containing sulfonic acids, and converting the resulting salts of formula I. into the free imidates of formula I.

2. The process as claimed in claim 1, wherein anhydrous hydrofluoric acid or trifluoromethanesulfonic acid is employed.

3. The process as claimed in claim 1, wherein anhydrous hydrofluoric acid is employed.

4. The process as claimed in claim 1, wherein a Lewis acid is employed additionally as a catalyst.

5. The process as claimed in claim 1, wherein a catalyst belonging to the group comprising antimony pentachloride, antimony trifluoride, phosphorus pentachloride, phosphorus trichloride, titaniumtetrachloride, iron (III) chloride, aluminum trichloride, zinc dichloride, boron trifluoride, boron trichloride, copper (I) chloride or tin (IV) chloride is employed additionally.

6. The process as claimed in claim 1, wherein a trichloromethyl aromatic compound or a mineral acid are employed additionally as a catalyst.

7. The process as claimed in claim 1, wherein the process is carried out within the temperature range from $-20°$ C. to $+200°$ C.

8. The process as claimed in claim 1, wherein the process is carried out within the temperature range from 50° to 150° C.

9. The process as claimed in claim 1, wherein a Lewis acid catalyst is added in an amount of 0.001 to 1 mole per mole of nitrile of the formula II.

10. The process as claimed in claim 1, wherein a trichloromethyl aromatic compound is added in an amount of 0.01 to 1 mole per mole of nitrile of the formula II.

11. The process as claimed in claim 1, wherein, in formula I,

R denotes $(C_1-C_{20})$-alkyl, phenyl which is substituted by $(C_1-C_6)$-alkyl, $(C_1-C_6)$-halogenoalkyl, halogen or hydroxyl, $(C_3-C_7)$-cycloalkyl which can be halogenated, or pyridyl, pyrrolyl, furyl, thienyl or dioxotetrahydropyridyl, it being possible for these heterocyclic radicals to be substituted by $(C_1-C_4)$-alkyl, $(C_1-C_6)$-halogenoalkyl, $(C_1-C_6)$-alkoxy, $(C_1-C_6)$-halogeno-alkoxy or halogen, $R^1$ denotes $(C_1-C_{12})$-alkyl which can be monosubstituted or polysubstituted by halogen and/or monosubstituted by nitro or carboxyl, phenyl which can be substituted by $(C_1-C_6)$-alkyl, $(C_1-C_6)$-halogenoalkyl, $(C_1-C_6)$-alkoxy, $(C_1-C_6)$-halogenoalkoxy or halogen, $(C_5-C_6)$-cycloalkyl, naphthyl or $(C_3-C_6)$-alkenyl or pyridyl or benzthiazolyl both of which can be substituted by $(C_1-C_6)$-alkyl or halogen, and X denotes O or S.

12. The process as claimed in claim 1, wherein the resulting salts of formula I are converted into the free imidates of formula I with the addition of bases.

13. The process as claimed in claim 1, further comprising subsequently converting the free imidates of formula I into the salts or acid addition compounds thereof.

* * * * *